United States Patent [19]
Hagihara

[11] Patent Number: 5,535,758
[45] Date of Patent: Jul. 16, 1996

[54] AIDING DEVICE FOR MEN WITH SEXUAL DYSFUNCTION

[76] Inventor: Hideo Hagihara, 3-9-15 Yumura Kofu, Yamanashi, Japan

[21] Appl. No.: 521,284

[22] Filed: Aug. 29, 1995

Related U.S. Application Data

[63] Continuation of Ser. No. 227,574, Apr. 14, 1995, abandoned, which is a continuation of Ser. No. 959,965, Oct. 13, 1992, abandoned.

[51] Int. Cl.$^6$ .................................................. A61F 5/00
[52] U.S. Cl. .................................................. 128/897; 600/38
[58] Field of Search .................................. 600/38–39, 41; 128/842, 844, 897–8

[56] References Cited

U.S. PATENT DOCUMENTS

| | | |
|---|---|---|
| 602,917 | 4/1898 | Scheinkman . |
| 844,798 | 2/1907 | Hawley . |
| 2,705,951 | 4/1955 | Crowner ................. 128/844 |
| 3,131,691 | 5/1964 | Scott . |
| 4,182,319 | 1/1980 | Scott ....................... 128/79 |
| 4,432,357 | 2/1984 | Pomeranz ............... 128/79 |
| 4,498,466 | 2/1985 | Pomeranz ............... 128/79 |
| 4,638,790 | 1/1987 | Conway et al. ......... 128/844 |
| 4,640,270 | 2/1987 | Chin ........................ 128/79 |
| 4,893,616 | 1/1990 | Immonon ................ 128/79 |
| 5,050,619 | 9/1991 | Ferguson ................ 128/842 X |
| 5,083,556 | 1/1992 | Osbon et al. ........... 600/39 |

*Primary Examiner*—Angela D. Sykes
*Assistant Examiner*—John P. Lacyk
*Attorney, Agent, or Firm*—Malin, Haley, DiMaggio & Crosby

[57] ABSTRACT

A device is disclosed for aiding men suffering from a sexual dysfunction such as impotency and premature ejaculation. In one embodiment, the device includes an external cylinder and an internal cylinder disposed within the external cylinder. The external cylinder resembles a normal erected human penis. The internal cylinder has a chamber area for receiving a non-erected human penis. In a second embodiment, the device includes an external cylinder and an internal cylinder disposed within the external cylinder. The external cylinder resembles a normal erected human penis. The internal cylinder has a chamber area for receiving an erected human penis. In a final embodiment, the device includes an external cylinder, an internal cylinder initially disposed within the external cylinder and a cap initially operatively associated with the internal cylinder. In this embodiment, once the device has been fitted only the external cylinder remains attached to the human penis and allows the penis head to be exposed.

6 Claims, 6 Drawing Sheets

AIDING DEVICE FOR MEN WITH SEXUAL DYSFUNCTION

This application is a continuation of application Ser. No. 08/227,574, filed Apr. 14, 1995, now abandoned; which is a continuation of application Ser. No. 07/959,965, filed Oct. 13, 1992, now abandoned.

BACKGROUND OF THE INVENTION

1. Field of the Invention

This invention relates generally to sexual aid devices and more particularly to a device for aiding men with impotency and premature ejaculation problems.

2. Background of the Invention

Reportedly a steadily growing number of men have suffered from sexual dysfunction like impotence in recent years, due to nervous disorders (as stress, depression, etc.) or physical disorders (as diabetes, hypertension, etc.) as well as old age. This reveals a cross section of a complex and highly developed modern society. In North European countries and the U.S., sexual dysfunction is now widely recognized as a serious social problem facing complex, modern societies.

Men suffering from sexual dysfunction have so far been thought to need either medical therapy (medication) or surgical therapy (surgery). However, such procedures are quite often very expensive and have not been proven to successful in every case. Furthermore, the use of medication or surgery also involves risks and the chance of side-effects as well as possible complications.

Impotency, as well as premature ejaculation, over a period of time can cause a serious strain on even the best of marriages. As such, impotency is reportedly creating many matrimonial troubles and problems throughout the world. Thus, there exist a need in the prior for an sexual aid device which overcomes the problems of impotency and premature ejaculation, while at the same time does not require surgery or medication to overcome such problems. It is, therefore, to the effective resolution of the aforementioned problems and shortcomings that the present invention is directed.

SUMMARY OF THE INVENTION

Generally, the present invention relates to a sexual aid device for use with men having either impotency or premature ejaculation problems. The instant device in all embodiments consists of an external cylinder and an internal cylinder which fits into the external cylinder.

The first embodiment is specially used for men suffering from erectile dysfunction due to old age or nervous disorders or from physical dysfunctions such as diabetes. In this first embodiment, the external cylinder is made to be of the same size as a normal erected penis, while the internal cylinder is made as to fit the normal penis size of an impotent man. Once fitted the sexual aid device of the first embodiment closely mimics a human erect penis, thus enabling the impotent male to satisfy his female partner, as if the male had no impotency problems at all.

The second embodiment is designed to restore potency in men who have a mild case of impotence due to stress of work or old age. In this second embodiment, the external cylinder is made up of a conical fixing body with an adjusting cap fixed on the body and the internal cylinder consists of a conical body and cap. Only the external cylinder serves as an aiding device for men with sexual dysfunction. However, the internal cylinder is required in order to fit the penis into the external cylinder. In this embodiment, the insertion of the penis is facilitated by baring the glans and fixing the penis from the outside. This embodiment stimulates erection and hastens recovery from impotence, due to the fact that after insertion, pressure produced in the vagina stimulates the bare glans as in natural intercourse.

The final embodiment is designed for use by men suffering from impotency, but is also specifically designed for use with men suffering from premature ejaculation. In this final embodiment, the internal cylinder is sized to fit a normal erect penis. However, the device is designed to prevent the stimulation of the erect penis by shutting the glans of the erect penis off from the clitoris. However, as the external cylinder is sized and shaped like a normal erect penis, the female partner can be fully satisfied. Once the female partner has been satisfied, the male partner can quickly remove the device and achieve satisfaction.

Thus the sexual aid device, as described in all three embodiments, overcomes the shortcomings of the prior art by allowing for sexual satisfaction of both partners, even when the male partner suffers from impotency or premature ejaculation.

Accordingly, the primary object of the present invention is to provide a sexual aid device which will assist satisfying a female partner when the male partner suffers from impotency.

It is another object of the present invention to provide a sexual aid device which will restore potency in a man who is suffering from a mild case of impotency.

It is yet another object of the present invention to provide a sexual aid device which will assist satisfying a female partner when the male partner suffers from premature ejaculation.

It is still another object of the present invention to provide a sexual aid device which will prevent ejaculation from a man suffering from premature ejaculation.

It is a further object of the present invention to provide a sexual aid device which closely mimics an erect human penis in touch, elasticity and sensible temperature.

It is an even further object of the present invention to assist a stagnant sexual relationship without the use of surgery or medication.

It is yet another object of the present invention to provide a sexual aid device which can quickly by attached or removed from a human penis.

It is yet another object of the present invention to provide a sexual aid device which can be easily cleaned and sterilized without causing damage to the device.

It is yet another object of the present invention to provide a sexual aid device for use with a human penis which does not cause any harm or side effects to the human penis.

It is yet another object of the present invention to provide a sexual aid device which is low in cost and easy to manufacture.

Other objects and advantages of this invention will become apparent from the following description taken in conjunction with the accompanying drawings wherein set forth, by way of illustration and example, certain embodiments of this invention. The drawings constitute a part of this specification and include exemplary embodiments of the present invention and illustrate various objects and features thereof.

BRIEF DESCRIPTION OF THE DRAWINGS

The invention may be better understood by reference to the drawings in which.

DETAILED DESCRIPTION OF THE PREFERRED EMBODIMENT

Figure 1:
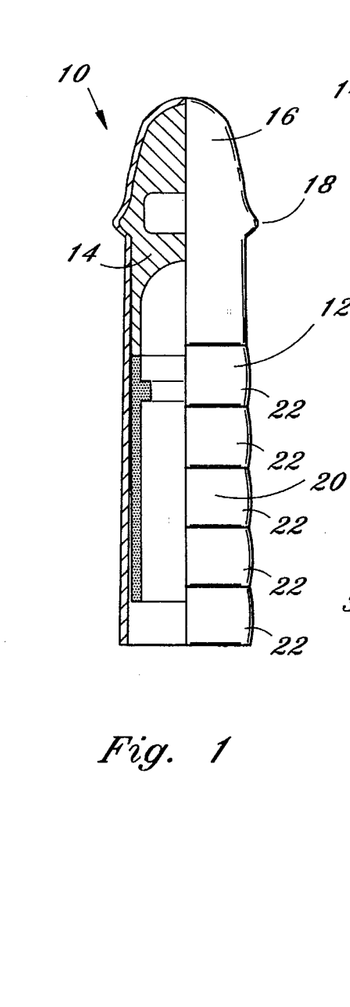
FIG. 1 is a perspective view of the first embodiment of the present invention with a portion of the external cylinder removed to illustrate the internal cylinder.
Figures 2, 3:
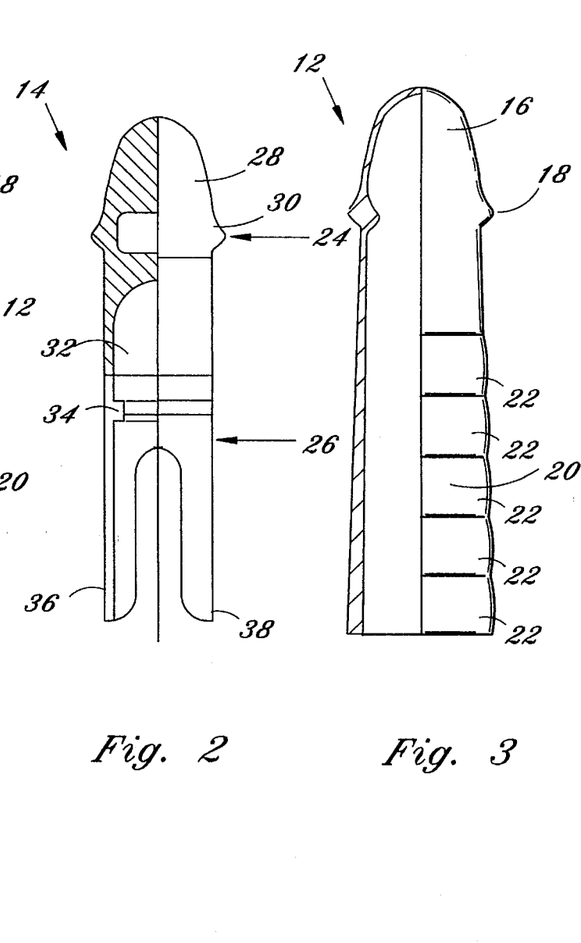
FIG. 2 is a perspective view of the internal cylinder of FIG. 1, with a portion of the internal cylinder removed to illustrate the interior of the internal cylinder.
FIG. 3 is a perspective view of the external cylinder of FIG. 1, with a portion of the external cylinder removed to illustrate the interior of the internal cylinder.
Figure 4:
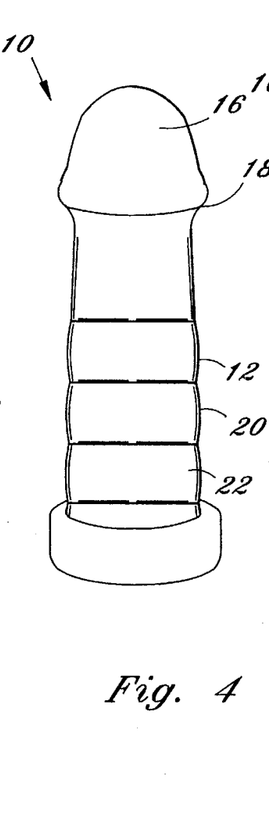
FIG. 4 is a perspective view of the invention of FIG. 1.
Figure 5:
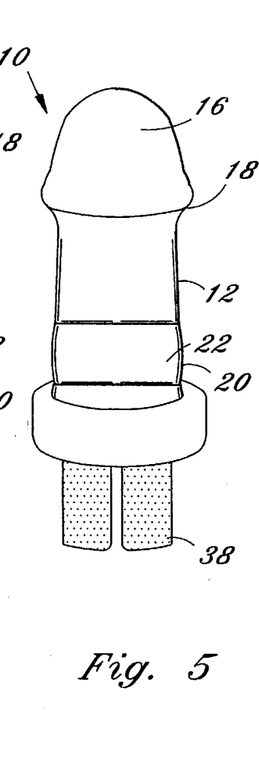
FIG. 5 is a perspective view of the invention of FIG. 1 with a portion of the external cylinder rolled up to expose the fixing wings of the internal cylinder.
Figure 6:
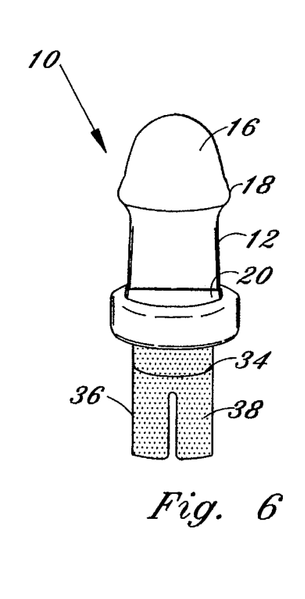
FIG. 6 is a perspective view of the invention of FIG. 1 with an additional portion of the external cylinder rolled up to further expose the internal cylinder.
Figure 7:
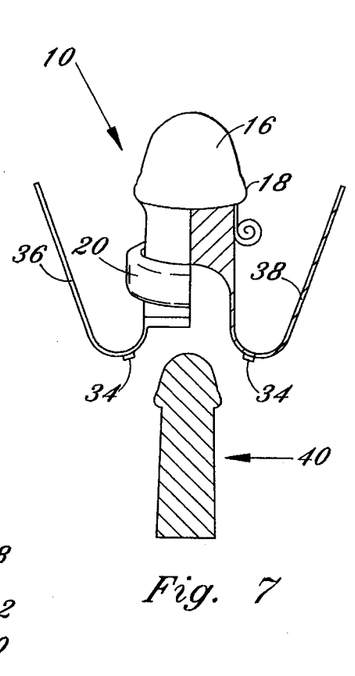
FIG. 7 is a perspective view of the invention of FIG. 1 showing the fixing wings of the internal cylinder folded back.
Figures 8, 9:
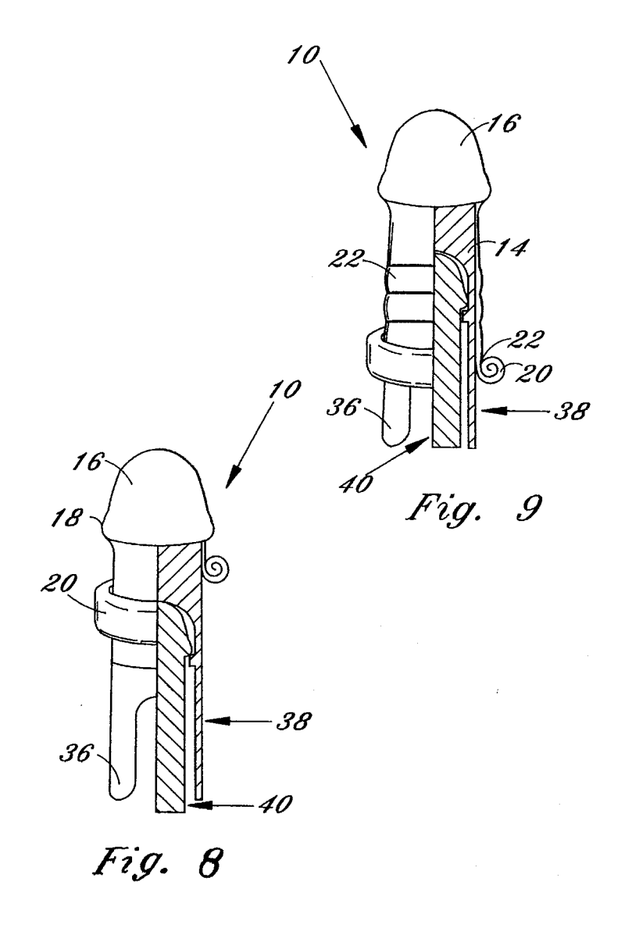
FIG. 8 is a perspective view of the invention of FIG. 1 showing the fixing wings returned to their original position and the male penis fitted within the internal cylinder.
FIG. 9 is a perspective view of the invention of FIG. 1 wherein the external cylinder has started to be rolled down from along the internal cylinder after the male penis has been fitted within the internal cylinder.

Referring now to the drawings, FIGS. 1–3 illustrate the first embodiment of the present invention. The instant invention, generally shown as device 10, consist of two cylinders, an external cylinder 12 and an internal cylinder 14. Internal cylinder 14 fits within external cylinder 12. Device 10 can be made of a material which is totally harmless to a man. Device 10 closely mimics and resembles a human penis, in touch, elasticity and sensible temperature. Without feeling any discomfort, a female partner can get nearly the same satisfaction out of the use of device 10 as out of natural intercourse with a man not suffering from impotency problems.

External cylinder 12 resembles the normal size of an erected human penis, whereas as internal cylinder 14 is constructed to fix or fit the penis of an impotent man. External cylinder 12 consists of three parts: a glans member 16, a glans ring member 18 and a wavy skin member 20. The front of wavy skin member 20 consist of several wavy steps 22, while its back is made to be thinner that glans member 16 and glans ring member 18.

Internal member 14 consists of two parts: an upper part 24 and a lower part 26. Upper part 24 consists of a glans member 28 and a glans ring member 30. Lower part 26 consists of a fitting or fixing chamber member 32, a fitting or fixing ring member 34 and two fixing or fitting wings 36 and 38.

FIG. 4–9 illustrate the operation of device 10. In operation, internal cylinder 14 is disposed within external cylinder 12. Initially, wavy skin member 20 is rolled up along internal cylinder 14 until the body of internal cylinder 14 is bared or exposed. Once bared, fixing wings 36 and 38 are folded back which also causes fixing ring 34 to expand open. The impotent penis 40 is then inserted within fixing chamber 32. Once inserted, fixing wings 36 and 38 are brought down to their original position thus, causing fixing ring 34 to securely retain penis 40 within internal cylinder 14. Lastly, wavy skin member 20 is rolled down to its original position. Wavy skin member 20 adheres closely to penis 40 by pressing wings 36 and 38 of internal cylinder 14 hard from the outside.

Device 10 increases the frictional coefficient between an impotent man and his female partner. Once device 10 is fitted to penis 40, it works in any position one could take during normal sexual activity, without coming off under any condition. After fitting, the male partner does not feel uncomfortable. Device 10 can be attached or removed within 15 to 20 seconds. No fixing band or fixing tape is required. After device 10 has been used, it can be washed in hot or cold water containing detergent or it can be sterilize by boiling, without changing the size or quality of the material. Device 10 is specially designed for men suffering from erectile dysfunction due to old age or nervous disorders as well as physical dysfunctions as diabetes, hypertension, etc.

Figure 10:
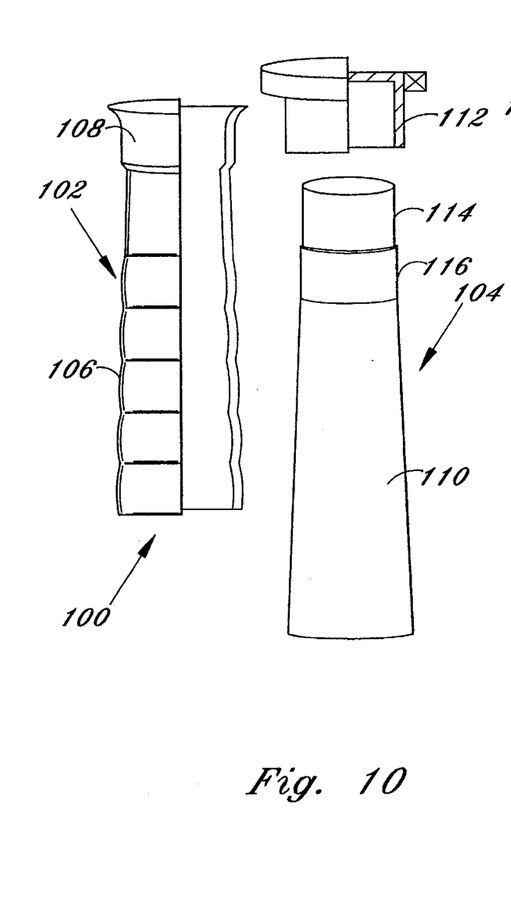
FIG. 10 is a perspective view of the second embodiment illustrating the components of the second embodiment individually.
Figure 11:
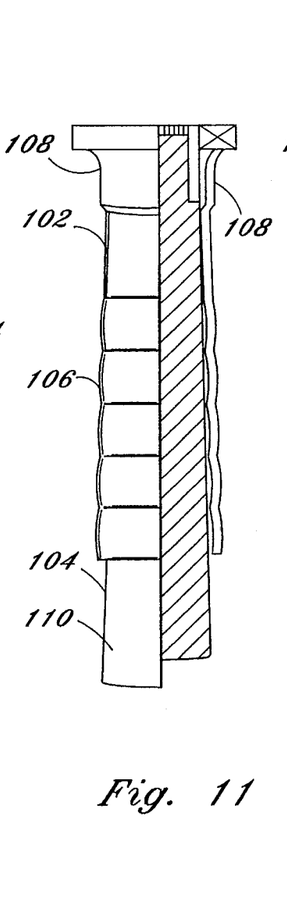
FIG. 11 is a perspective view of the invention of FIG. 10 with a portion of the external cylinder, internal cylinder and cap removed to expose the interior.

FIGS. 10 and 11 represent a second embodiment of the present invention. The second embodiment, generally shown as device 100, is designed primarily to restore potency in men who are suffering a mild case of impotency due to stress of work or old age. Device 100 consists of two cylinders, an external cylinder 102 and an internal cylinder 104. External cylinder 102 is made up of a conical fixing body 106 and an adjusting hood 108 attached to the top of conical fixing body 106. Internal cylinder 104 consists of a conical body 110 and a cap 112 resting on a cap setting point 114 and having a cap stopper 116. Only external cylinder 102 serves as an aiding device for men with sexual dysfunction. However, internal cylinder 104 is required in order to fit penis 118 into external cylinder 102.

Figures 12, 13:
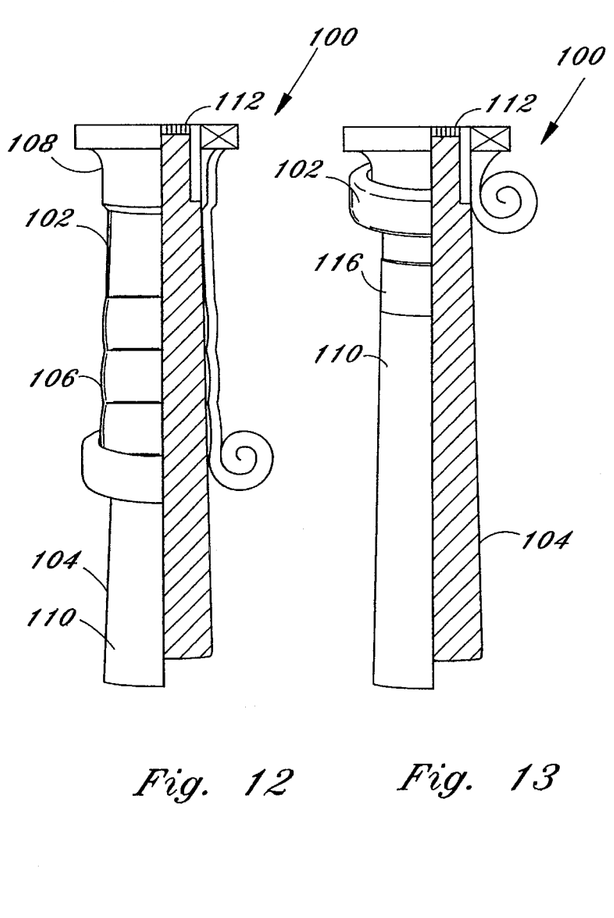
FIG. 12 is a perspective view of the invention of FIG. 10 illustrating the external cylinder partially rolled up along the internal cylinder.
FIG. 13 is a perspective view of the invention shown in FIG. 10 illustrating the external cylinder completely rolled up to the cap and off the internal cylinder.
Figures 14, 15, 16, 17, 18:
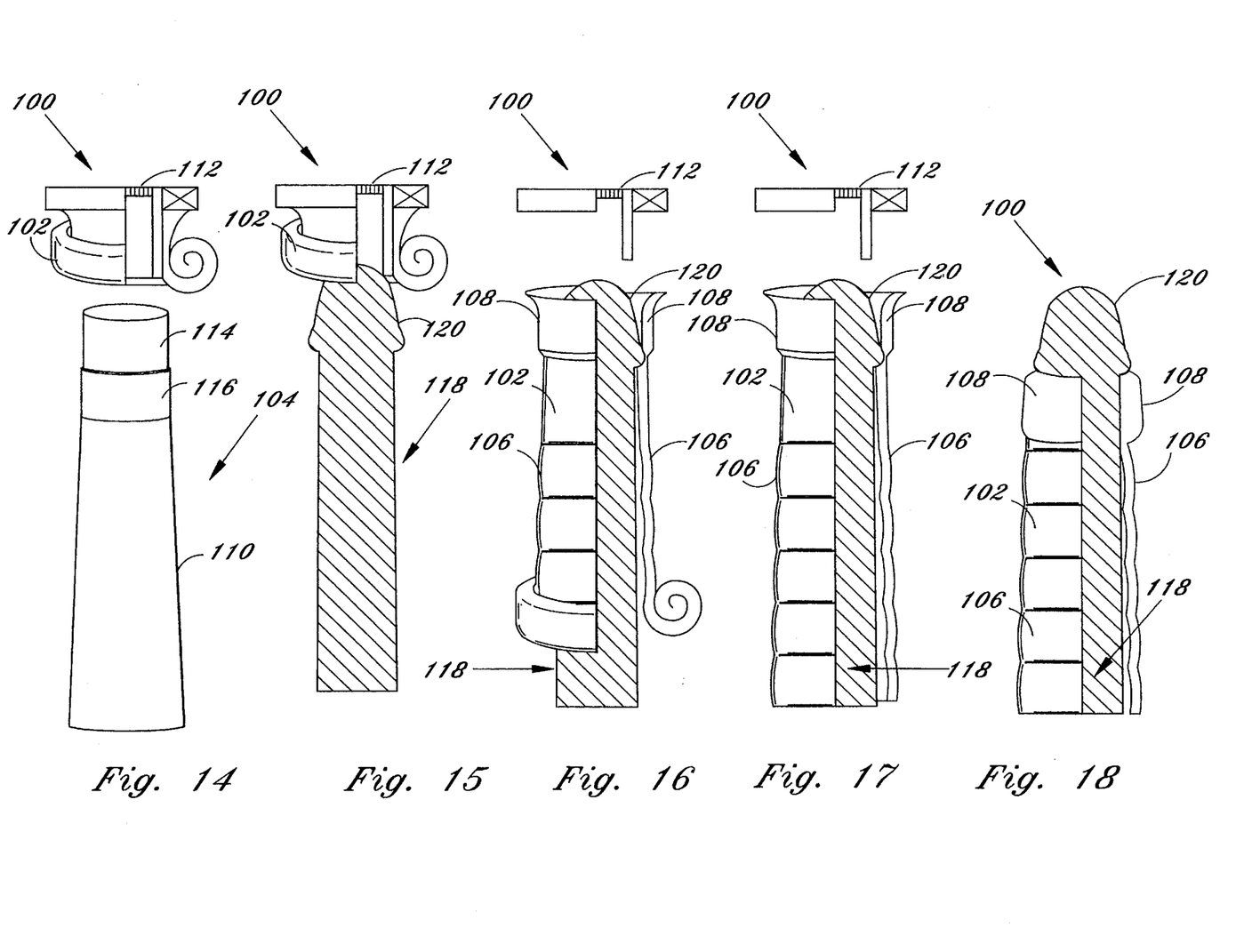
FIG. 14 is a perspective view of the invention shown in FIG. 10 illustrating the internal cylinder removed from the cap.
FIG. 15 is a perspective view of the invention shown in FIG. 10 with a portion of the external cylinder and cap removed to show the tip of the penis inserted within the cap.
FIG. 16 is a perspective view of the invention shown in FIG. 10 illustrating a portion of the external cylinder rolled down along the shaft of a human penis.
FIG. 17 is a perspective view of the invention shown in FIG. 10 showing the cap removed from the external cylinder and illustrating the external cylinder fully rolled down.
FIG. 18 is a perspective view of the invention shown in FIG. 10 illustrating the hood of the external cylinder folded over to fully expose the head of a human penis.
Figures 19, 20:
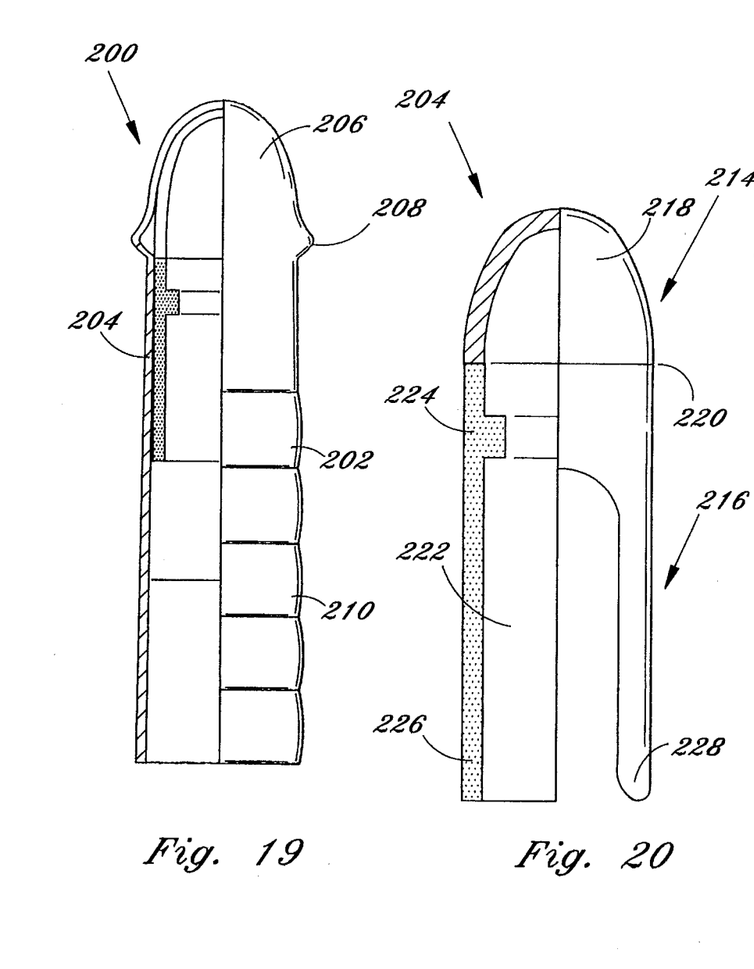
FIG. 19 is a perspective view of the third embodiment of the present invention with a portion of the external cylinder removed to illustrate the internal cylinder.
FIG. 20 is a perspective view of the internal cylinder of the invention shown in FIG. 19, with a portion of the internal cylinder removed to illustrate the interior of the internal cylinder.
Figure 21:
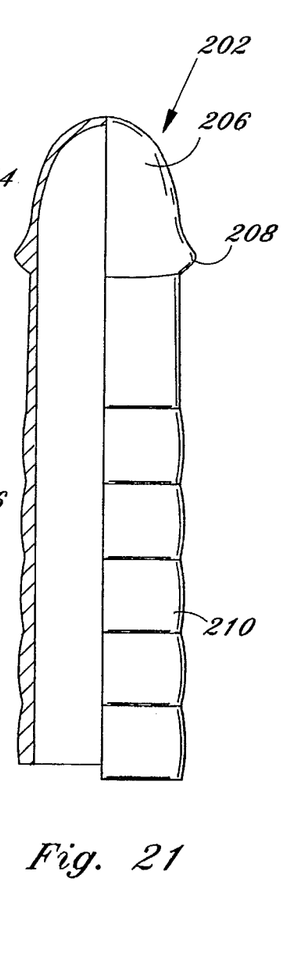
FIG. 21 is a perspective view of the external cylinder of the invention shown in FIG. 19, with a portion of the external cylinder removed to illustrate the interior of the internal cylinder.
Figure 22:
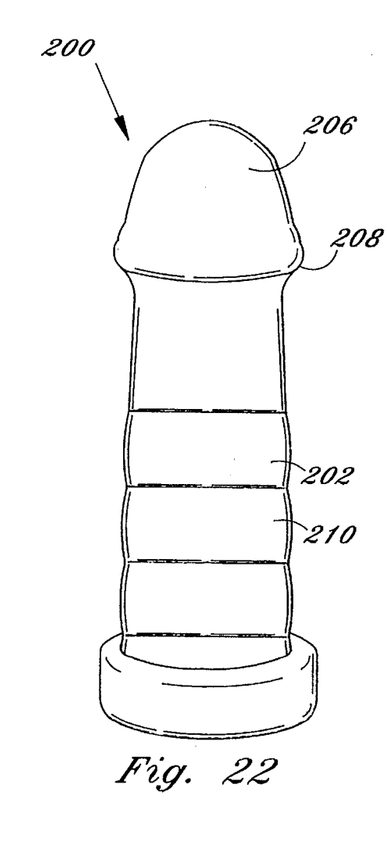
FIG. 22 is a perspective view of the invention shown in FIG. 19.
Figures 23, 24, 25, 26:
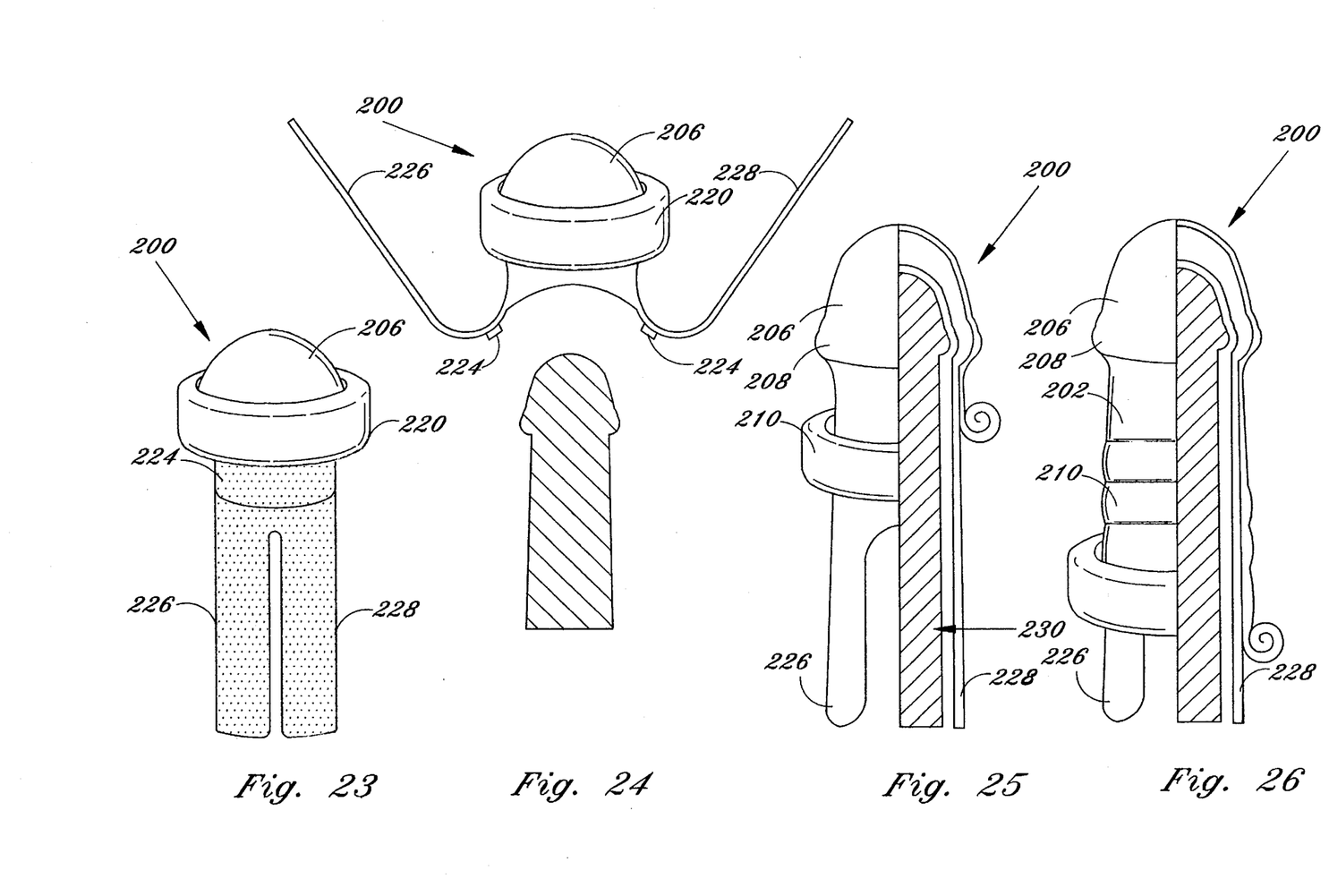
FIG. 23 is a perspective view of the invention shown in FIG. 19 with a portion of the external cylinder rolled up to expose the fixing wings of the internal cylinder.
FIG. 24 is a perspective view of the invention shown in FIG. 19 showing the fixing wings of the internal cylinder folded back.
FIG. 25 is a perspective view of the invention shown in FIG. 19 showing the fixing wings returned to their original position and the male penis fitted within the internal cylinder.
FIG. 26 is a perspective view of the invention shown in FIG. 19 wherein the external cylinder has started to be rolled down from along the internal cylinder after the male penis has been fitted within the internal cylinder.

FIGS. 12–18 illustrate the operation of device 100. In the initial operation, internal cylinder 104 is disposed within external cylinder 102. As seen in FIGS. 12 and 13, conical body 106 of external cylinder 102 is rolled up along internal cylinder 104 until conical body 106 is completely rolled up and disposed along cap 112. Conical body 110 of internal cylinder 104 is then removed or detached from cap 112. Penis 118 is then brought as closely as possible to cap 112 where wavy conical body 106 of external cylinder 102 is rolled down along the shaft of penis 118 to its original position. Once entirely unrolled, cap 112 is removed from engagement with adjusting hood 108. Finally, adjusting hood 108 is folded over so that the entire penis head 120 is uncovered or exposed. To remove device 100, adjusting hood 108 is folded back to its original position and device 100 is pulled off penis 118 slowly.

Device 100 facilitates the insertion of penis 118 by baring or exposing the glans of penis 18 and fixing penis 18 from the outside. Device 100 stimulates erection and hastens recovery from impotence, because after insertion, pressure produced in the vagina stimulates the bare glans of penis 118 as in natural intercourse.

Device 100 can be made of a material that and does not give any feeling of discomfort to the user and his partner. Device 100 can be attached or removed within 15 to 20 seconds. No fixing ban or fixing tape are required. After use, device 100 can be washed in hot or cold water containing detergent or it can be sterilized by boiling, without changing the size or the quality of the material.

FIG. 19–22 illustrate the final embodiment of the present invention, generally shown as device 200. Device 200 is primarily used where the male partner is suffering with premature ejaculation. Device 200 prevents the stimulation of an erected penis 230 by shutting erected penis 230 off from the outside.

Device 200 consists of an external cylinder 202 and an internal cylinder 204. Internal cylinder 204 is disposed within external cylinder 202. External cylinder 202 is similar to external cylinder 12 of the first embodiment and consists of a wavy skin member 210, glans member 206 and a glans ring member 208. Internal cylinder 204 consists of two parts: an upper part 214 and a lower part 216. Upper part 214 consists of a glans member 218 and a glans ring member 220. Lower part 216 consist of a fitting or fixing chamber member 222, a fitting or fixing ring member 224 and two fixing or fitting wings 226 and 228.

FIG. 22–26 illustrate the operation of device 200. In operation, internal cylinder 204 is disposed within external cylinder 202. Initially, wavy skin member 210 is rolled up along internal cylinder 204 until the body of internal cylinder 204 is bared or exposed. Once bared, fixing wings 226 and 228 are folded back which also causes fixing ring 224 to expand open. The erected penis 230 is then inserted within fixing chamber. Once inserted, fixing wings 226 and 228 are brought down to their original position thus, causing fixing ring 224 to securely retain penis 230 within internal cylinder 204. Lastly, wavy skin member 210 is rolled down to its original position. Wavy skin member 210 adheres closely to penis 230 by pressing wings 226 and 228 of internal cylinder 204 hard from the outside.

Once device 200 is fitted to penis 230, it works in any position one could take during normal sexual activity, without coming off under any condition. After fitting, the male partner does not feel uncomfortable. Device 200 can be attached or removed within 15 to 20 seconds. No fixing band or fixing tape is required. After device 200 has been used, it can be washed in hot or cold water containing detergent or it can be sterilize by boiling, without changing the size or quality of the material.

It is to be understood that while we have illustrated and described certain forms of my invention, it is not to be limited to the specific forms or arrangement of parts herein described and shown. It will be apparent to those skilled in the art that various changes may be made without departing from the scope of the invention and the invention is not to be considered limited to what is shown in the drawings and described in the specification.

What is claimed is:

1. A sexual aid device for aiding persons with a sexual disfunction comprising:

an external cylinder having a body portion and resembling an erected human penis, and including an external glans member, an external glans ring member and an external skin member, each of said external glans member, external glans ring member and external skin member simulating the actual appearance of said an internal cylinder disposed within said external cylinder, said internal cylinder including a body portion defining an internal chamber therein for receiving a penis, said internal chamber including an internal glans member for covering the glans, an internal glans ring member for covering an area behind the glans and an internal skin member for covering an area behind the external ring member; and at least one resilient retaining member depending from said body portion, said member bendable away from said body portion and frictionally engaging said penis when it is within said internal chamber.

2. The sexual aid device of claim 1 wherein said external chamber is sized for receiving a flaccid penis.

3. The sexual aid device of claim 1 wherein said external chamber is sized for receiving an erected human penis.

4. A method of placing a sexual aid device on a human penis, said device for assisting a man suffering from a sexual dysfunction, said device having an external cylinder and an internal cylinder, said external cylinder having a resilient body portion and moveable between extended and compressed positions, said external cylinder resembling an erected human penis, said internal cylinder disposed within said external cylinder, said internal cylinder having a body portion and a plurality of flexible retaining members depending from said body portion and moveable between static and expanded positions, the body portion and retaining members defining an internal chamber for receiving a human penis, comprising the steps of:

(a) rolling an edge of the resilient body portion of said external cylinder from its extended position along said internal cylinder into said compressed position, so said plurality of retaining members are fully exposed;

(b) folding said flexible retaining members from their static position outwardly from said internal cylinder to said expanded position;

(c) inserting a human penis within said internal chamber;

(d) folding said flexible retaining members back to their static position;

(e) unrolling the resilient body portion of said external cylinder edge down along said internal cylinder to its extended position.

5. The method of claim 5 further comprising the step of pressing said retaining members and the body portion of said external cylinder adjacent said retaining members to allow said body portion to closely adhere to the penis.

6. A method placing a sexual aid device on a glans penis, said device for assisting a man suffering from a sexual dysfunction, said device having an external cylinder, internal cylinder and a cap, said external cylinder having a body portion and a hood member operatively associated with the body portion, said internal cylinder initially disposed within said external cylinder, said internal cylinder having a conical body shape portion and a first and second end, said cap initially operatively associated with the first end of said internal cylinder, comprising the steps of:

(a) rolling an edge of the body portion of said external cylinder along said internal cylinder until the body portion of said external cylinder is completely removed from said internal cylinder and disposed around said cap;

(b) removing said internal cylinder from said cap;

(c) rolling said edge of body portion of said external cylinder down along a penis, said penis having a head portion;

(d) removing said cap from said external cylinder; and (e) folding the hood member onto the body portion of said external cylinder to completely expose the head portion.

* * * * *